(12) United States Patent
Ermann

(10) Patent No.: US 8,563,766 B2
(45) Date of Patent: Oct. 22, 2013

(54) INDANE DERIVATIVES FOR USE AS INTERMEDIATES

(75) Inventor: Peter Hans Ermann, Regensburg (DE)

(73) Assignee: DSM Pharma Chemicals, Regensburg (DE)

( * ) Notice: Subject to any disclaimer, the term of this patent is extended or adjusted under 35 U.S.C. 154(b) by 0 days.

(21) Appl. No.: 13/386,741

(22) PCT Filed: Jul. 22, 2010

(86) PCT No.: PCT/EP2010/060669
§ 371 (c)(1),
(2), (4) Date: Apr. 10, 2012

(87) PCT Pub. No.: WO2011/009928
PCT Pub. Date: Jan. 27, 2011

(65) Prior Publication Data
US 2012/0190881 A1    Jul. 26, 2012

(30) Foreign Application Priority Data
Jul. 24, 2009   (EP) ..................... 09166390

(51) Int. Cl.
*C07C 69/753*    (2006.01)
*C07C 45/54*     (2006.01)
*C07C 45/65*     (2006.01)

(52) U.S. Cl.
USPC .......................................... 560/51; 568/314

(58) Field of Classification Search
None
See application file for complete search history.

(56) References Cited

FOREIGN PATENT DOCUMENTS

WO   WO 2004/063168    7/2004

OTHER PUBLICATIONS

International Search Report for PCT/EP2010/060669, mailed Dec. 9, 2010.
Written Opinion for PCT/EP2010/060669, mailed Dec. 9, 2010.
Trogen et al., "Synthesis and Structure of 1,5—and 1,7—Dihydro-s-indacenes", *Acta Chemica Scandanavia B*, vol. 33, 1979, pp. 109-112.
Tu et al., "Total Synthesis of 4-Demethoxy-13-dihydro-8-nordaumomycin", *J. Org. Chem*, vol. 52, No. 25, 1987, pp. 5624-5627.

*Primary Examiner* — Brian J Davis
(74) *Attorney, Agent, or Firm* — Nixon & Vanderhye P.C.

(57) ABSTRACT

A compound of Formula (4), wherein each X is independently fluorine or chlorine; n is 1 or 2; $R^1$ is $C_3$-$C_8$ alkyl, phenyl or benzyl; and $R^2$ is $C_1$-$C_6$ alkyl; and its production and use.

(4)

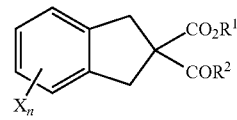

9 Claims, No Drawings

INDANE DERIVATIVES FOR USE AS INTERMEDIATES

This application is the U.S. national phase of International Application No. PCT/EP2010/060669 filed 22 Jul. 2010 which designated the U.S. and claims priority to EP 09166390.6 filed 24 Jul. 2009, the entire contents of each of which are hereby incorporated by reference.

The present invention relates to a compound of Formula (4),

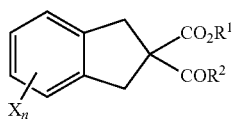

(4)

wherein each X is independently fluorine or chlorine; n is 1 or 2; $R^1$ is $C_3$-$C_8$ alkyl, phenyl or benzyl; and $R^2$ is $C_1$-$C_6$ alkyl; and its production and use.

The compounds of Formula (4) are useful as intermediates in the synthesis of $\alpha_2$ adrenoceptor antagonists, such as 4-(2-ethyl-5-fluoroindan-2-yl)-1H-imidazole (fipamezole) and 4-(5-fluoroindan-2-yl)-1H-imidazole, both of which are described in EP0618906.

The reaction of the compound of Formula (4) to any of the above $\alpha_2$ adrenoceptor antagonists can proceed through a compound of Formula (7),

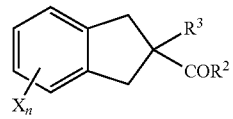

(7)

wherein X, n and $R^2$ are as defined above, and $R^3$ is $C_1$-$C_{12}$ alkyl.

EP1581504 describes a synthetic route suitable for converting 2-ethyl-5-fluoro-2-acetylindan to 4-(2-ethyl-5-fluoroindan-2-yl)-1H-imidazole. An unhalogenated analogue, 2-ethyl-2-acetylindan, is an intermediate in the synthesis of the $\alpha_2$ adrenoceptor antagonist 4-(2-ethyl-indan-2-yl)-1H-imidazole (atipamezole) as described by Wong and Gluchowski in Synthesis (2) 139-40, 1995.

An economic synthetic route to 4-(2-alkyl-haloindan-2-yl)-1H-imidazoles, for example 4-(2-ethyl-5-fluoroindan-2-yl)-1H-imidazole, is desired. Accordingly an object of the present invention is the production of a compound of Formula (7). A further object of the present invention is the production of a crystalline solid starting material for a compound of Formula (7) which is suitable as a registered intermediate or registered starting material for pharmaceutical synthesis. A still further object of the present invention is to avoid the use of harmful reagents.

Accordingly, the present invention provides a compound of Formula (4),

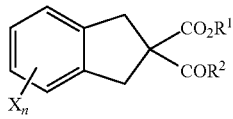

(4)

wherein each X is independently fluorine or chlorine; n is 1 or 2; $R^1$ is $C_3$-$C_8$ alkyl, phenyl or benzyl; and $R^2$ is $C_1$-$C_6$ alkyl.

X is typically fluorine.

Typically n is 1.

Preferably X is fluorine and n is 1. More preferably the fluorine is located at the 5-position of the indanyl core.

$R^1$ is typically $C_3$-$C_6$ alkyl or benzyl. Preferably $R^1$ is tert-butyl or benzyl. More preferably $R^1$ is tert-butyl.

$R^2$ is typically $C_1$-$C_4$ alkyl. Preferably it is methyl or ethyl, more preferably methyl.

The present invention further provides a process for the production of a compound of Formula (4), comprising reacting a compound of Formula (2) with a compound of Formula (3),

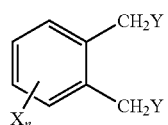

(2)

(3)

$R^2C(O)CH_2CO_2R^1$ wherein X, n, $R^1$ and $R^2$ are as defined above and Y is chlorine or bromine.

In another embodiment, the present invention provides use of a compound of Formula (4) as defined above, in the production of a compound of Formula (6),

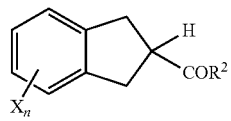

(6)

wherein X, n, and $R^2$ are as defined above, by cleaving the moiety —$OR^1$ from the compound of Formula (4), followed by decarboxylation.

A $C_3$-$C_8$ alkyl radical is preferably $C_3$-$C_6$ alkyl radical. Preferred examples are iso-propyl, n-butyl, sec-butyl, tert-butyl, pentanyl, hexanyl.

As used herein an alkyl radical may be unsubstituted or substituted. Typical substituents are halogen. Preferably it is unsubstituted.

As used herein a phenyl radical may be unsubstituted or substituted. Typical substituents are halogen or nitro.

As used herein a benzyl radical may be unsubstituted or substituted. Typical substituents are halogen or nitro. Preferably it is unsubstituted.

Preferred halogens are chlorine or bromine.

Preferably, the compounds of Formula (4) are in crystalline form. Typically crystalline forms may be produced in good purity, and easily stored and transported. Accordingly, compounds of Formula (4) are suitable as registered intermediates or registered starting materials in a pharmaceutical synthesis. Preferred compounds of Formula (4) are those which readily crystallize.

Further preferred compounds of Formula (4) are those that are readily converted to a compound of Formula (6). Such compounds include those wherein $R^1$ is $C_3$-$C_6$ alkyl or benzyl. More preferably each X is fluorine; $R^1$ is tert-butyl or benzyl; and $R^2$ is methyl. A particularly preferred compound of Formula (4) is 2-acetyl-2-(benzyloxycarbonyl)-5-fluoro-indane or 2-acetyl-2-(tert-butoxycarbonyl)-5-fluoro-indane.

2-acetyl-2-(tert-butoxycarbonyl)-5-fluoro-indane is particularly advantageous because it is easily crystallized. For example it has a significantly higher melting point than the analogous 2-acetyl-2-(benzyloxycarbonyl)-5-fluoro-indane. Therefore, crystallization of 2-acetyl-2-(tert-butoxycarbonyl)-5-fluoro-indane is possible from the reaction mixture of the compounds of Formula (2) and (3) used as reagents to produce it, wherein the compound of Formula (2) is produced in situ and not isolated. This is especially advantageous because 1,2-bis-(bromomethyl)-4-fluoro-benzene (a compound of Formula (2)) is a powerful lachrymator. Preferably its isolation should be avoided.

A preferred process of producing a compound of Formula (2) is by in situ bromination or chlorination of a compound of Formula (1),

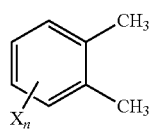

(1)

wherein X and n are as defined above. Preferably, each X is fluorine. Preferably n is 1. Most preferably the compound of Formula (1) is 3,4-dimethylfluorobenzene.

Methods of bromination are known in the art and include use of N-bromosuccinimide (NBS). Methods of chorination are also known in the art and include that described in EP0343560.

A complication with the in situ generation of the compound of Formula (1) from the compound of Formula (2) is that impurities may be produced; for example, over- or under-bromination or chlorination of one or both of the methyl groups of the toluene moiety. These impurities can react with the compound of Formula (3) to produce by-products. A particular advantage of the high melting point and good crystallization of 2-acetyl-2-(tert-butoxycarbonyl)-5-fluoro-indane is that it can be obtained selectively in crystalline form and high purity from a solution which includes such by-products. For example, there is a wider choice of solvents available for crystallization and no need for column chromatography to isolate 2-acetyl-2-(tert-butoxycarbonyl)-5-fluoro-indane.

Preferably in the process of producing a compound of Formula (4), $R^1$ is $C_3$-$C_6$ alkyl or benzyl. More preferably each X is fluorine; $R^1$ is tert-butyl or benzyl; and $R^2$ is methyl.

The compound of Formula (4) may be converted to the compound of Formula (6) by cleaving the moiety —$R^1$, followed by decarboxylation. The moiety —$OR^1$ may be cleaved by either hydrolysis or hydrogenation. Hydrolysis is preferably acid hydrolysis. Typically it is carried out at elevated temperature. Hydrolysis is preferred when $R^1$ is $C_3$-$C_8$ alkyl. Hydrogenation is typically carried out using gaseous hydrogen and a catalyst, for example a supported palladium catalyst. A suitable solvent is THF. Hydrogenation is preferred when $R^1$ is benzyl. Decarboxylation is typically spontaneous.

Typically, in the process of producing a compound of formula (6), $R^1$ is $C_3$-$C_6$ alkyl or benzyl. More preferably $R^1$ is tert-butyl or benzyl, $R^2$ is methyl, and X is fluorine.

A preferred further use of the compound of Formula (4) is alkylation of a compound of Formula (6) to form a compound of Formula (7),

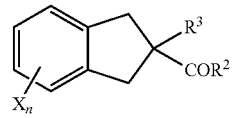

(7)

wherein X and $R^2$ are as defined above, and $R^3$ is $C_1$-$C_{12}$ alkyl.

Alkylation may be achieved, for example, by reaction of the compound of Formula (6) with an alkylhalide ($R^3$-hal) in the presence of a base. For example $R^3$-iodide ($R^3$I) may be used in the presence of $^t$BuOK.

Typically $R^3$ is $C_1$-$C_6$ alkyl. Preferably, $R^3$ is ethyl. Accordingly, preferably alkylation is by ethyl iodide (EtI) in the presence of $^t$BuOK. A suitable solvent for alkylation is THF.

The present invention is illustrated but not limited to the following examples.

EXAMPLES

Example 1

2-acetyl-2-(benzyloxycarbonyl)-5-fluoro-indane

To 5 g of 1,2-bis-(bromomethyl)-4-fluoro-benzene in 100 ml of methylethylketone were added 14.7 g of potassium carbonate followed by 4.1 g of benzyl acetoacetate. The mixture was stirred for 16 h at ambient temperature. 100 ml of water were added. The phases were separated and the aqueous phase was extracted once with 50 ml of methylethylketone. The combined organic phases were evaporated to give 6.2 g of crude product as an oil. The crude product was crystallized from cold heptane and from cold methanol. Melt.p. 55° C. $^1$HNMR: δ=2.16 ppm (s, 3H); 3.50 ppm (AB, 2H); 3.53 ppm (AB, 2H); 5.22 (s, 2H); 6.88 ppm (m, 2H); 7.12 ppm (dd, 1H) 7.30-7.42 ppm (m, 5H).

Example 2

2-acetyl-2-(tert-butoxycarbonyl)-5-fluoro-indane

To 10 g of 1,2-bis-(bromomethyl)-4-fluoro-benzene in 200 ml of methylethylketone were added 29.4 g of potassium carbonate followed by 6.7 g of tert-butyl acetoacetate. The mixture was stirred for 16 h at ambient temperature. 200 ml of water were added. The phases were separated and the aqueous phase was extracted once with 100 ml of methylethylketone. The combined organic phases were washed once with 100 ml of water. The solvent was evaporated and to the resulting oil were added 20 ml of methanol. After 1 h stirring at ambient temperature the product was filtered off, washed with 2×5 ml of methanol and dried. Yield: 6.2 g. Melt.p. 73° C. $^1$HNMR: δ=1.48 ppm (s, 9H); 2.25 ppm (s, 3H); 3.44 ppm (AB, 2H); 3.47 (AB, 2H); 6.87 ppm (m, 2H); 7.12 ppm (dd, 1H)

Example 3

2-acetyl-2-(tert-butoxycarbonyl)-5-fluoro-indane 2-acetyl-2-(tert-butoxycarbonyl)-5-fluoro-indane was also prepared from 3,4-dimethylfluorobenzene via crude 1,2-bis- (bromomethyl)-4-fluoro-benzene without purification of the crude 1,2-bis-(bromomethyl)-4-fluoro-benzene before reaction with tert-butyl acetoacetate. Reaction conditions for both steps were the same as described above. In this case the product was finally crystallized from ethanol/water.

Example 4

2-acetyl-5-fluoro-2-indane from 2-acetyl-2-(tert-butoxycarbonyl)-5-fluoro-indane A solution of 1 g of 2-acetyl-2-(tert-butoxycarbonyl)-5-fluoro-indane in 10 ml of formic acid was warmed to 40° C. and stirred at 40° C. for 2 hours. In-process control showed complete conversion to 2-acetyl-5-fluoro-2-indane. 20 ml of water were added, then the pH was adjusted to 7 by addition of sodium hydroxide solution. The mixture was extracted three times with each 40 ml of methyl tert-butylether (MTBE). The organic phase was washed once with 40 ml of water. Evaporation of the organic phase gave 0.5 g of the product as an oil. The product solidifes in the deep freezer.

Example 5

2-acetyl-5-fluoro-2-indane from 2-acetyl-2-(benzyloxycarbonyl)-5-fluoro-indane

To a solution of 6 g of crude 2-acetyl-2-(benzylcarbonyl)-5-fluoro-indane in 60 ml of THF was added 0.6 g of 10% Pd/C (50% water wet) and hydrogen was bubbled through the solution at atmospheric pressure. After 2 h, the mixture was warmed to 40° C. and hydrogenation was continued. More Pd/C catalyst was added in 2 portions (0.3 g and 0.6 g). After a total of 7 h, the catalyst was filtered off, and was washed with 18 ml of THF. The combined filtrates were washed with 18 ml of halfsaturated $NaHCO_3$ solution and with 18 ml of water. Evaporation of the solvent gave 1.66 g of crude product as an oil.

The invention claimed is:

1. A compound of Formula (4),

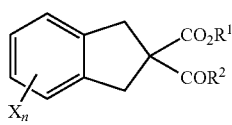

(4)

wherein each X is independently fluorine or chlorine; n is 1 or 2; $R^1$ is $C_3$-$C_8$ alkyl, phenyl or benzyl; and $R^2$ is $C_1$-$C_6$ alkyl.

2. A compound according to claim 1, wherein each X is fluorine; $R^1$ is tert-butyl or benzyl; and $R^2$ is methyl.

3. A compound according to claim 1, which is 2-acetyl-2-(benzyloxycarbonyl)-5-fluoro-indane or 2-acetyl-2-(tert-butoxycarbonyl)-5-fluoro-indane.

4. A compound according to claim 1, in crystalline form.

5. A process for the production of a compound of Formula (4),

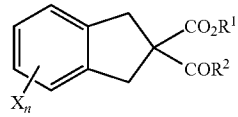

(4)

which comprises reacting a compound of Formula (2),

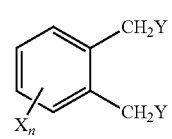

(2)

with a compound of Formula (3), $R^2C(O)CH_2CO_2R^1$ (3)

wherein each X is independently fluorine or chlorine; n is 1 or 2; $R^1$ is $C_3$-$C_8$ alkyl, phenyl or benzyl; $R^2$ is $C_1$-$C_6$ alkyl; and Y is chlorine or bromine.

6. A process according to claim 5, further comprising producing the compound of Formula (2) in situ by bromination or chlorination of a compound of Formula (1),

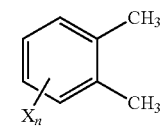

(1)

wherein X and n are as defined previously.

7. A process according to claim 5, wherein each X is fluorine; $R^1$ is tert-butyl or benzyl; $R^2$ is methyl and Y is bromine.

8. A process for the production of a compound of Formula (6),

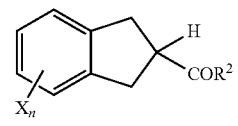

(6)

which comprises cleaving a moiety —$OR^1$ from a compound of Formula (4),

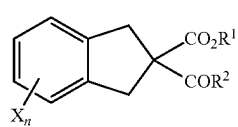

(4)

followed by decarboxylation to obtain the compound of Formula (6), wherein each X is independently fluorine or chlorine; n is 1 or 2; $R^1$ is $C_3$-$C_8$ alkyl, phenyl or benzyl; $R^2$ is $C_1$-$C_6$ alkyl.

9. The process according to claim 8, further comprising alkylation of the compound of Formula (6) to form a compound of Formula (7),

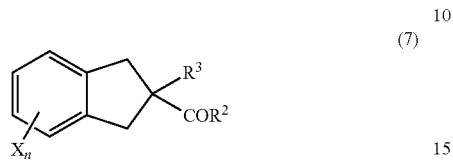

(7)

wherein X, n and $R^2$ are as defined previously, and $R^3$ is $C_1$-$C_{12}$ alkyl.

* * * * *